United States Patent [19]

Chen

[11] 4,384,584

[45] May 24, 1983

[54] METHOD AND MEANS FOR ESOPHAGEAL FEEDING

[76] Inventor: Allen S. Chen, 16400 N. Park Dr., Southfield, Mich. 48075

[21] Appl. No.: 315,936

[22] Filed: Oct. 28, 1981

[51] Int. Cl.³ .................... A61M 25/00; A61B 17/34
[52] U.S. Cl. ...................................... 604/28; 604/98; 604/100
[58] Field of Search ............... 128/348, 349 R, 349 B, 128/1 R, 1.3, 305.3, 207.15, 207.16, 207.17, 303 R, 200.26, 6, 7, 8

[56] References Cited

U.S. PATENT DOCUMENTS

| 1,767,267 | 6/1930 | Wappler | 128/7 X |
|---|---|---|---|
| 3,100,482 | 8/1963 | Hett | 128/6 |
| 3,162,190 | 12/1964 | Gizzo | 128/6 |
| 3,324,847 | 6/1967 | Zoumboulis | 128/1.2 |
| 3,640,281 | 2/1972 | Robertson | 128/347 |
| 3,656,485 | 4/1972 | Robertson | 128/349 R |
| 3,656,486 | 4/1972 | Robertson | 128/349 R |
| 3,760,797 | 9/1973 | Stauffer | 128/6 |
| 3,856,020 | 12/1974 | Kovac | 128/349 R |
| 3,885,561 | 5/1975 | Cami | 128/349 R X |
| 3,897,775 | 8/1975 | Furihata | 128/6 |
| 3,961,632 | 6/1976 | Moossun | 128/348 X |
| 3,985,139 | 10/1976 | Penar | 128/349 B |
| 4,057,065 | 11/1977 | Thow | 128/349 B X |
| 4,096,862 | 6/1978 | DeLuca | 128/348 |
| 4,201,199 | 5/1980 | Smith | 128/6 X |
| 4,231,365 | 11/1980 | Scarberry | 128/207.15 |
| 4,244,362 | 1/1981 | Anderson | 128/1.3 X |
| 4,248,214 | 2/1981 | Hannah et al. | 128/349 R X |
| 4,311,148 | 1/1982 | Courtney et al. | 128/348 |

*Primary Examiner*—Richard J. Apley
*Assistant Examiner*—Michelle N. Lester
*Attorney, Agent, or Firm*—Barnes, Kisselle, Raisch, Choate, Whittemore & Hulbert

[57] ABSTRACT

A naso-esophageal catheter is provided with an inflatable balloon at its distal end and a signal-emitting device is located within the balloon so that the location of the distal end of the catheter can be determined when it is advanced into the patient's esophagus. After the catheter has been advanced into the patient's esophagus, the balloon is inflated. Thereafter, a trans-cervical esophageal catheter is directed through the patient's neck towards the center of the inflated balloon. After the balloon has been punctured the naso-esophageal catheter is withdrawn and the patient can then be fed with liquid nutrients through the trans-cervical esophageal catheter.

11 Claims, 13 Drawing Figures

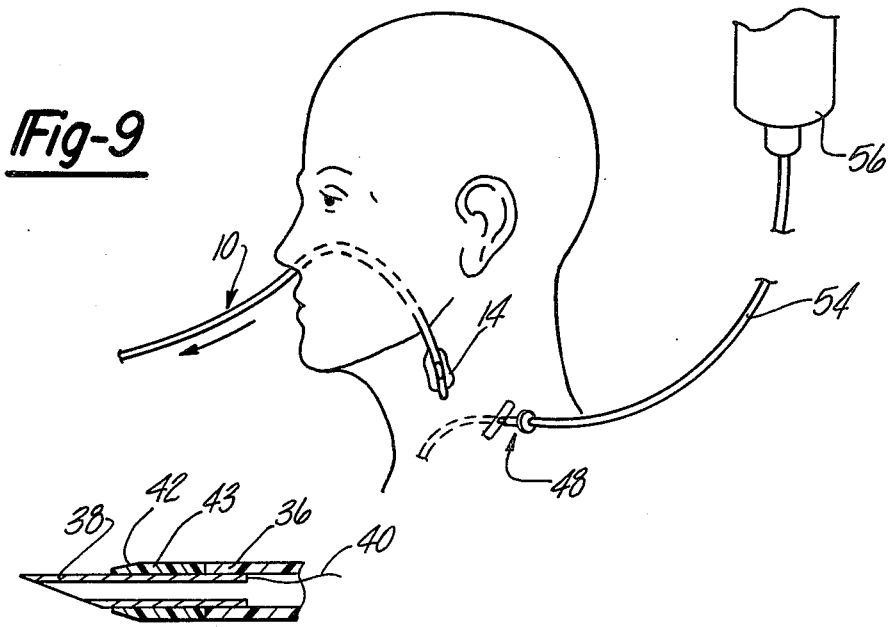
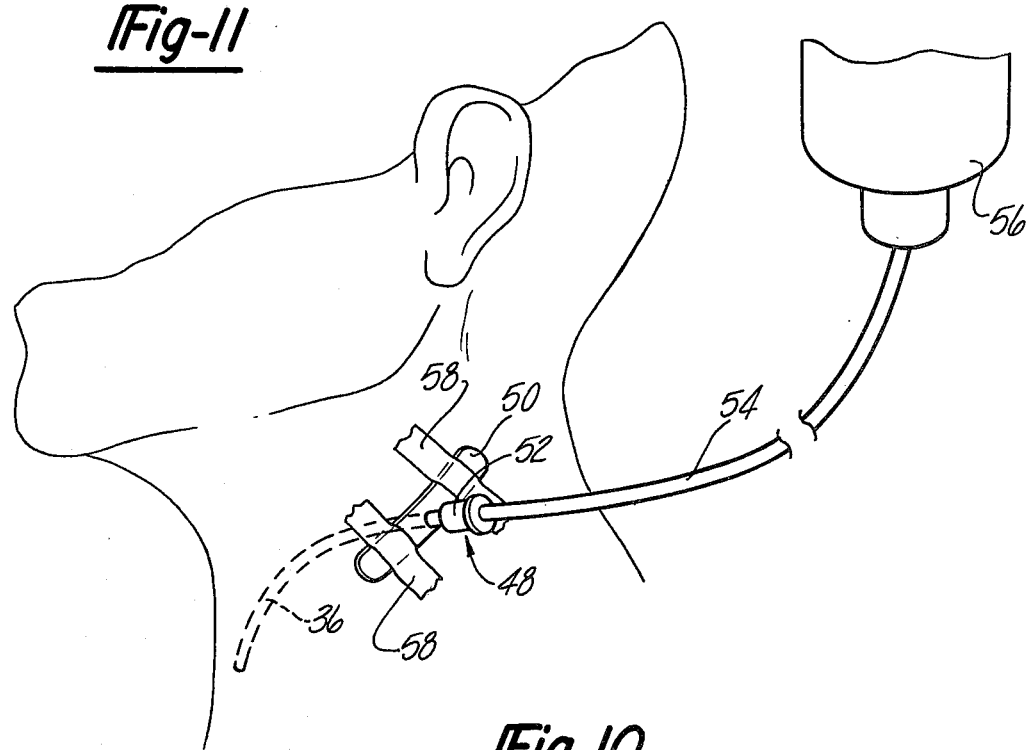

METHOD AND MEANS FOR ESOPHAGEAL FEEDING

This invention relates generally to a method and means for esophageal feeding and, more particularly, to a method and means for inserting an esophageal catheter directly through the neck of a patient.

Naso-gastric feeding is frequently employed in cases of chronic debilitant patients, such as those suffering from terminal cancer, extensive burns, etc. However, prolonged use of naso-gastric tube feeding frequently results in aspiration pneumonia, which is the most common cause of death following such prolonged feeding. While abdominal feeding by means of gastrostomy avoids some of the discomforts and problems encountered in naso-gastric feeding, this procedure involves major abdominal surgery and is avoided whenever possible.

The primary object of this invention is to provide a simple and safe procedure for esophageal feeding patients which avoids the problems and dangers encountered with present-day methods of such feeding.

More specifically, the present invention has for its object a method for esophageal feeding of patients by admitting nutrient liquids directly into the patient's esophagus by means of a trans-cervical esophageal catheter inserted into the esophagus through the patient's neck.

The invention also has for its object the provision of an effective means and method for inserting a trans-cervical esophageal catheter into the esophagus through the patient's neck.

Other objects, features and advantages of the present invention will become apparent from the following description and accompanying drawings, in which:

FIGS. 9 and 10 illustrate the trans-cervical esophageal catheter secured in feeding position on the patient's neck;

FIG. 11 is a fragmentary sectional view of the distal end of the trans-cervical esophageal catheter;

Figure 1:
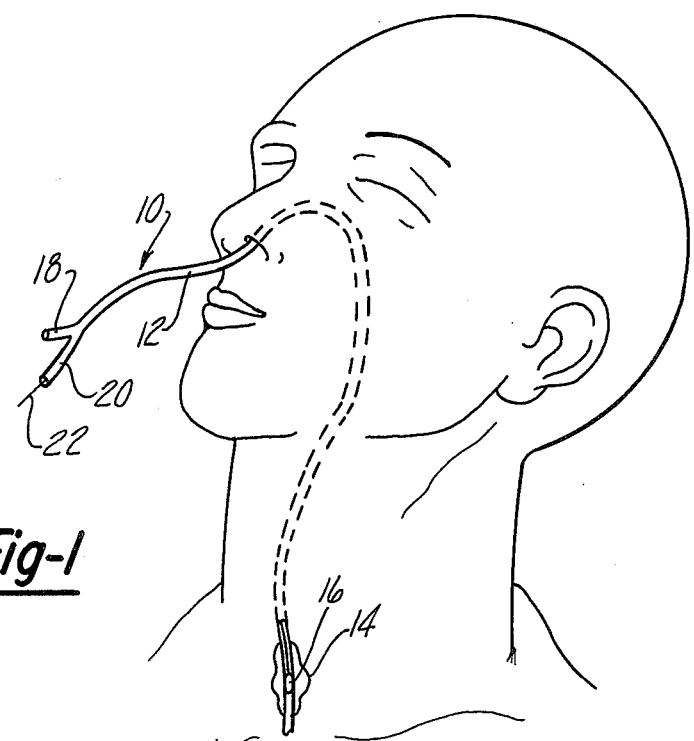
FIG. 1 and 2 are views showing the manner in which the naso-esophageal catheter of the present invention is advanced through the nasal passage into the patient's esophagus.
Figure 2:
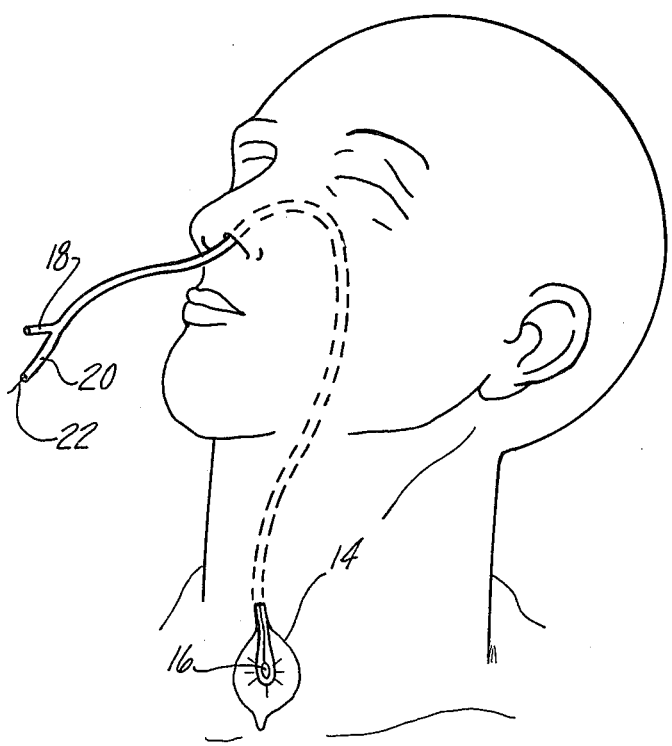

Referring to FIGS. 1 through 8, the naso-esophageal catheter of the present invention, generally designated 10, is in some respects similar to a conventional Foley catheter. It comprises a small diameter flexible tube 12, preferably made of transparent plastic, such as vinyl chloride, and having a thin inflatable latex balloon 14 sealed thereon adjacent its distal end. However, it differs from a conventional Foley catheter in that the portion of the catheter surrounded by the balloon 14 has a signal-emitting member 16 located therein. The distal end of tube 12 can extend beyond balloon 14 as shown in FIG. 1 or can terminate within balloon 14 just beyond the signal-emitting device 16 as shown in FIG. 2.

The portion of tube 12 surrounded by balloon 14 is formed with one or more small openings therein (not shown) to permit inflation of the balloon by directing fluid into the proximal end of the catheter. If the signal-emitting member 16 is of the electrically-energized type, the proximal end of tube 12 is formed as a Y with two branches 18,20 so that the balloon 14 may be inflated by directing fluid into the branch 18 and conductors 22, or the like, can be extended through the branch 20 to a suitable source of electric energy.

Figure 12:
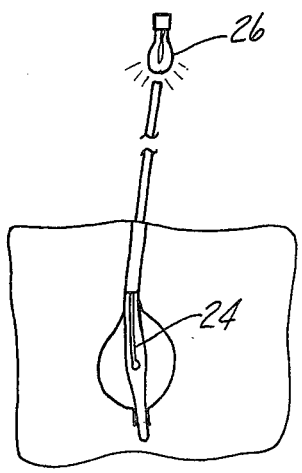
FIGS. 12 and 13 are fragmentary views illustrating modified forms of a naso-esophageal catheter according to the present invention.

The signal-emitting member 16 is preferably in the form of a small light bulb, such as shown in FIG. 2, of sufficient intensity so that the light spot created thereby is visible through the catheter from exteriorly of the patient's neck when the catheter is inserted through the patient's nasal passageway into the esophagus. s an alternative to a light bulb as the signal-emitting member, a bundle of optic fibers 24 may be employed which is energized by a light source 26 at or beyond the branch 20 through which the bundle of fibers extends. The optic fiber signal-emitting member is illustrated in FIG. 12. As a second alternative, the signal-emitting member can be in the form of a piece of magnetic material 28 supported within tube 12 by any suitable means, such as by a wire 30. The location of the magnetic member 28 from exteriorly of the patient's neck can be determined by using a conventional magnetized indicator unit 32.

Figure 13:
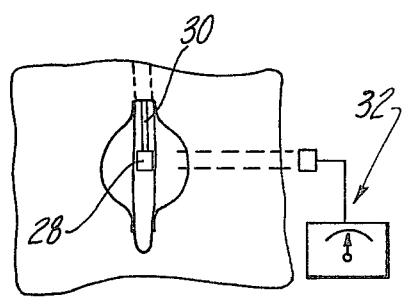
Figure 3:
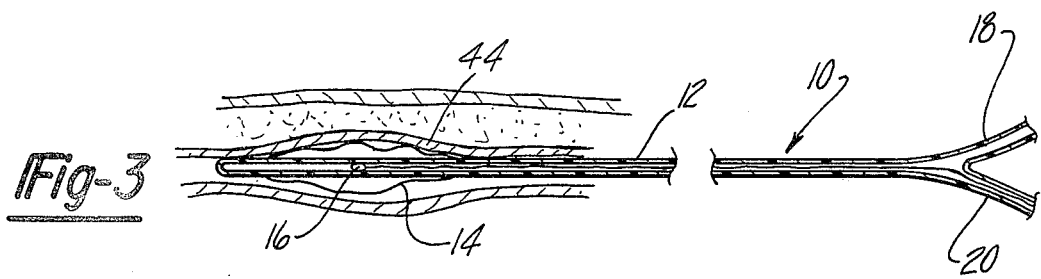
FIGS. 3 through 8 are sectional views showing progressive steps illustrating the manner in which a trans-cervical esophageal catheter is inserted into the patient's esophagus through his neck.
Figure 4:
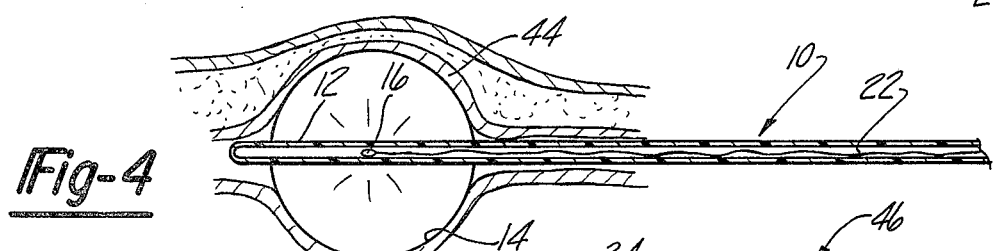

In use, the naso-esophageal catheter 10, which may have a length of approximately 18 inches, is inserted through the left side of the patient's nose and advanced until the distal end thereof is located within the patient's esophagus. While the length of the exposed portion of the catheter will give some indication as to the general location of the distal end thereof, if necessary, this can be accurately determined by noting the location of the signal-emitting member 16, which in the case of a light bulb or a bundle of optic fibers illuminated at its end, is visible, expecially in a darkened room through the patient's neck. In the case of a magnetic signal-emitting member such as shown at 28 in FIG. 13, its location can be determined by the magnetized indicator 32. In any event, when it has been determined that the distal end of the catheter is located within the patient's esophagus, the balloon 14 is inflated. This is preferably accomplished by directing a colored fluid, such as sterile water, into the inlet branch 18 of the catheter. Normally, when the balloon 14 is inflated, its location will be evidenced by the appearance of a bump on the exterior of the patient's neck. In the case of excessively fleshy patients where the location of the bump may not be apparent, the location of the balloon can, in any event, be determined by ascertaining the location of the signal-emitting member 16.

Since the signal-emitting member 16 is located approximately at the center of the inflated balloon and since the balloon is located generally in the patient's esophagus, it then becomes a relatively simple procedure to insert a trans-cervical esophageal catheter through the patient's neck so that the distal end thereof penetrates the inflated balloon 14. The trans-cervical esophageal catheter, which is generally designated 34 in the drawings, may be of conventional construction. It comprises a soft flexible plastic tube 36 which is preferably made of a transparent vinyl chloride and has a hollow needle 38 projecting from the distal end thereof as shown in FIG. 11. Needle 38 preferably has a wire 40 attached thereto and extending through the tube to the proximal end thereof to enable withdrawal of the needle from within the tube. The distal end of tube 36 is preferably tapered as at 42 to facilitate penetration of the catheter through the skin tissues in the patient's neck. In accordance with a preferred embodiment of the invention, the end portion of tube 36 having the tapered section 40 is formed as a short section 43 which is frictionally retained in place by its engagement with the outer periphery of needle 38.

Figure 5:
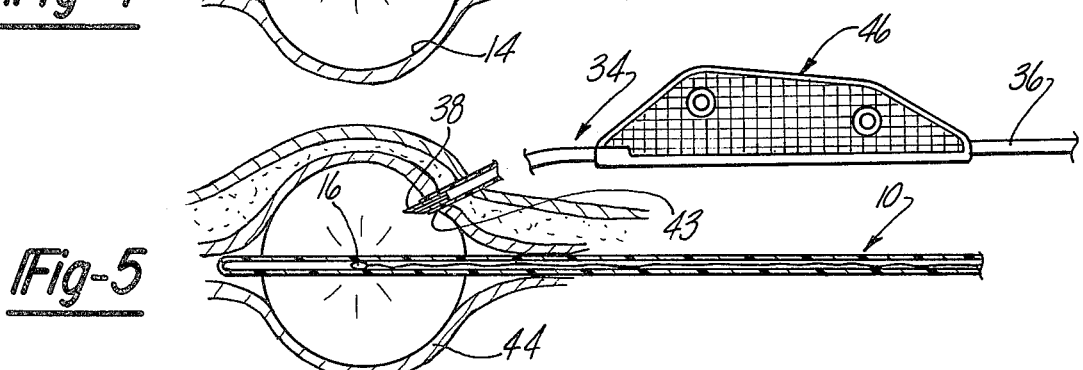
Figure 6:
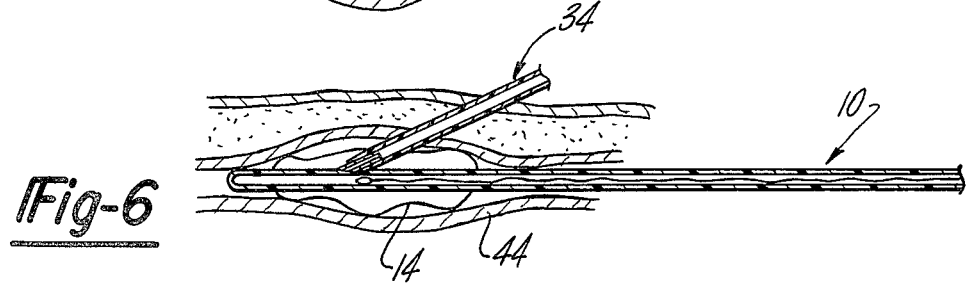
Figure 7:
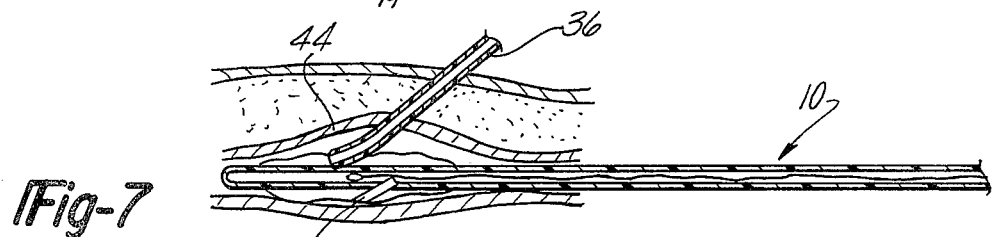
Figure 8:
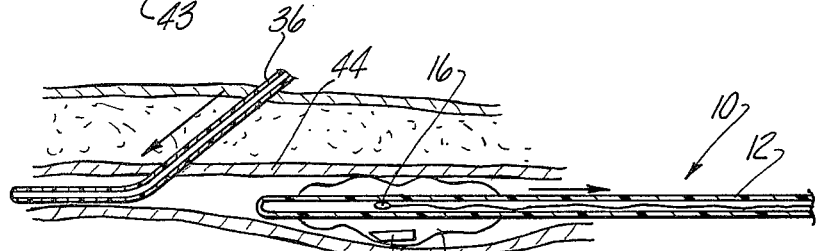

Referring to FIG. 5, after the balloon 14 on the catheter 10 is located in the esophagus 44 and is inflated, the distal end of catheter 34 is directed through the patient's neck in a downwardly direction towards the location of the signal-emitting member 16. This is facilitated by the conventional manually manipulatable clamp 46 on tube 36. Penetration of the needle 38 through the balloon 14 is promptly evidenced by the flow of colored fluid through the tube 36 of catheter 34. Since this fluid is under at least slight pressure within the inflated balloon, when the balloon is punctured, colored fluid will flow through and drip from the end of the tube and serve as an indication that the end of needle 38 is indeed disposed within the balloon. As soon as the fluid begins to flow through tube 36 the user advances the catheter further (FIG. 6) to insure that the end portion of the tube itself has advanced a sufficient extent into the esophagus. Thereafter, the needle 38 is withdrawn from within tube 36. When the needle is withdrawn, the tapered tip section 43 falls freely off of the end of tube 36 and remains within the deflated balloon 14. In order to insure that an adequate length of tube 36 is located within the patient's esophagus, both catheters 10 and 34 are simultaneously advanced further to the extent of about 3 to 5 centimeters. At this time, since the tip section 43 has been dislodged from the end of tube 36, the distal end of the tube is blunt and is therefore not apt to puncture or injure any tissue. However, when the above-described procedure is followed, the blunt end of tube 36 is still located within the deflated balloon. Therefore, before the catheter 10 can be safely withdrawn, it is necessary to disengage the distal end of tube 36 from within the balloon. This is accomplished by advancing the catheter 10 further (for example, 2 to 3 centimeters) relative to tube 36 to thereby relatively displace the end of tube 36 from within the balloon. Thereafter the catheter 10 can be safely extracted with the assurance that the distal end portion of tube 36 is properly located within the patient's esophagus (FIG. 8).

As shown in FIG. 10, the proximal end of tube 36 has connected thereto a tubular fitting 48 provided with a soft flexible base 50 and a stem 52. A liquid feed tube 54 connected with a liquid nutrient container 56 is adapted to be inserted into one end of stem 52 and the proximal end of tube 36 is adapted to be telescopically engaged with the other end of stem 52. The base 50 is adapted to be attached to the patient's neck by adhesive strips 58 to hold the assembly in place. In this manner the patient can be fed nutrient liquids over a prolonged period of time and the problems frequently encountered with naso-gastric feeding and gastrastomy feeding are avoided.

I claim:

1. The method of inserting a catheter type feeding tube into a patient's esophagus which comprises inserting a soft flexible first catheter into the oral or nasal passage of the patient and advancing the catheter until its distal end is located within the esophagus, said catheter comprising a tube having a collapsed balloon adjacent its distal end adapted to be inflated by fluid directed through a passageway in the catheter extending from within the balloon to the proximal end of the catheter, inflating the balloon to expand the surrounding portion of the esophagus, determining the location of the expanded portion of the esophagus on the exterior surface of the patient's neck, penetrating at said location through the patient's neck and into the expanded esophagus and balloon with a second catheter comprising a tube provided with a projecting needle at its distal end to collapse the balloon and simultaneously position the distal end of the second catheter within the esophagus, retracting the needle from the second catheter and, thereafter, disengaging the distal end of the second catheter from within the balloon and completely withdrawing the first catheter through the nasal or oral passageway in the patient whereby the proximal end of the second catheter is adapted to be connected to a source of liquid nutrient for conducting it into the patient's esophagus.

2. The method called for in claim 1 wherein the second catheter is advanced further into the esophagus after the balloon is collapsed.

3. The method called for in claim 1 wherein the first and second catheters are advanced further into the esophagus after the balloon is collapsed.

4. The method called for in claim 1 wherein the second catheter is directed through said location in the patient's neck and into the inflated balloon in a direction inclined downwardly into the esophagus.

5. The method called for in claim 4 wherein the first catheter is advanced further into the esophagus relative to the second catheter after the balloon is collapsed to disengage the distal end of the second catheter from within the balloon.

6. The method called for in claim 5 wherein the second catheter is advanced further into the esophagus before the needle is retracted.

7. The method called for in claim 1 wherein the balloon is inflated with a liquid which, when the balloon is penetrated by said needle, flows through the second catheter to visibly indicate that the balloon has been punctured.

8. The method called for in claim 7 wherein the liquid is colored and the determination that the balloon has been punctured is visibly indicated through the tube of the second catheter.

9. The method called for in claim 1 wherein said first catheter has a signal-emitting member in said balloon which enables determination of the location of the balloon from exteriorly of the patient's neck.

10. The method called for in claim 9 wherein the signal-emitting member comprises a light source and the determination of the location of the distal end of the first catheter within the esophagus is made by visually observing said light source exteriorly of the patient's neck.

11. The method called for in claim 9 wherein said signal-emitting member comprises a magnetic body and the determination of the location of the distal end of the first catheter within the esophagus is accomplished by utilizing a magnetic indicator.

* * * * *